(12) United States Patent
Cocker et al.

(10) Patent No.: US 12,343,470 B2
(45) Date of Patent: Jul. 1, 2025

(54) DRY POWDER INHALER

(71) Applicant: PHILIP MORRIS PRODUCTS S.A., Neuchâtel (CH)

(72) Inventors: Robin Craig Cocker, Derby (GB); Ben Alexander King, Oundle (GB); Christopher Iain Davidson, Cambridge (GB); Paul Mutti, Spilsby (GB); Alex Stenzler, Long Beach, CA (US); Steve Han, Huntington Beach, CA (US); James Tibbatts, Cambridge (GB)

(73) Assignee: Philip Morris Products S.A., Neuchâtel (CH)

( * ) Notice: Subject to any disclaimer, the term of this patent is extended or adjusted under 35 U.S.C. 154(b) by 997 days.

(21) Appl. No.: 17/422,845

(22) PCT Filed: Jan. 13, 2020

(86) PCT No.: PCT/IB2020/050235
§ 371 (c)(1),
(2) Date: Jul. 14, 2021

(87) PCT Pub. No.: WO2020/148633
PCT Pub. Date: Jul. 23, 2020

(65) Prior Publication Data
US 2021/0402113 A1    Dec. 30, 2021

(30) Foreign Application Priority Data
Jan. 14, 2019    (EP) ...................................... 19151686

(51) Int. Cl.
*A61M 15/00*    (2006.01)
*A61M 15/06*    (2006.01)

(52) U.S. Cl.
CPC .... *A61M 15/0066* (2014.02); *A61M 15/0023* (2014.02); *A61M 15/06* (2013.01); *A61M 2202/064* (2013.01)

(58) Field of Classification Search
CPC .......... A61M 15/0066; A61M 15/0023; A61M 15/06; A61M 2202/064; A61M 2209/06;
(Continued)

(56) References Cited

U.S. PATENT DOCUMENTS

| | | | |
|---|---|---|---|
| 2,587,215 | A | 2/1952 | Priestly |
| 2,590,832 | A | 3/1952 | Brown |

(Continued)

FOREIGN PATENT DOCUMENTS

| | | |
|---|---|---|
| CA | 2093809 | 2/1993 |
| CN | 101437562 A | 5/2009 |

(Continued)

OTHER PUBLICATIONS

Chinese Office Action for CN Application No. 202080007220.0 issued by the China National Intellectual Property Administration; Jan. 3, 2022; pgs. including English translation.

(Continued)

*Primary Examiner* — Justine R Yu
*Assistant Examiner* — Matthew R Moon
(74) *Attorney, Agent, or Firm* — Mueting Raasch Group

(57) ABSTRACT

The present invention provides dry powder inhaler (DPI) devices (100) for dispensing dry powder and methods for using the same. The DPI devices feature vortex mechanisms for directing air in a turbulent manner sufficient to entrain an amount of a dry powder dose for delivery into a user's lungs. The DPI devices feature replaceable dry powder cartridges (200). The DPI devices also feature a retractable configu- (Continued)

ration for storage and for accidental dispensing of dry powder. The DPI devices dispense dry powder in controlled dosages.

19 Claims, 13 Drawing Sheets

(58) Field of Classification Search
CPC .......... A61M 15/0028; A61M 15/0065; A61M 11/002; A61M 15/002; A61M 15/0048; A61M 15/005; A24F 42/20; A24F 42/60; A24F 7/00
See application file for complete search history.

(56) References Cited

U.S. PATENT DOCUMENTS

| | | | |
|---|---|---|---|
| 2,642,063 A | 6/1953 | Brown | |
| 3,008,609 A | 11/1961 | Sessions | |
| 5,542,411 A | 8/1996 | Rex | |
| 5,562,918 A | 10/1996 | Stimpson | |
| 5,699,789 A | 12/1997 | Hendricks | |
| 6,089,228 A * | 7/2000 | Smith | A61M 15/0036 128/203.15 |
| 6,234,169 B1 | 5/2001 | Bulbrook et al. | |
| 6,273,086 B1 * | 8/2001 | Ohki | A61M 15/0033 128/205.21 |
| 6,371,111 B1 * | 4/2002 | Ohki | A61M 15/003 128/203.23 |
| 7,503,324 B2 | 3/2009 | Barney et al. | |
| 8,668,928 B2 | 3/2014 | Rand | |
| 10,716,904 B2 | 7/2020 | Tibbatts et al. | |
| 10,828,435 B2 | 11/2020 | Yamada et al. | |
| 2003/0172928 A1 * | 9/2003 | Rand | A61M 15/0023 128/203.15 |
| 2004/0236282 A1 | 11/2004 | Braithwaite | |
| 2007/0209661 A1 | 9/2007 | Smyth | |
| 2009/0013994 A1 * | 1/2009 | Jones | A61M 15/0061 128/200.23 |
| 2009/0235930 A1 | 9/2009 | Young et al. | |
| 2010/0000530 A1 * | 1/2010 | Jauernig | A61M 11/002 128/203.15 |
| 2014/0190473 A1 | 7/2014 | Haindl | |
| 2014/0373838 A1 * | 12/2014 | Herder | A61M 15/0091 128/203.15 |
| 2016/0346488 A1 * | 12/2016 | Beller | A61M 11/002 |
| 2020/0187562 A1 * | 6/2020 | Rogan | A61M 15/0023 |

FOREIGN PATENT DOCUMENTS

| | | |
|---|---|---|
| CN | 104984451 | 10/2015 |
| EP | 1923087 | 3/2009 |
| EP | 2617450 | 7/2013 |
| GB | 2133385 A | 7/1984 |
| RU | 2281124 | 5/2006 |
| WO | 18188 | 10/1992 |
| WO | 16748 | 9/1993 |
| WO | 017595 | 3/2001 |
| WO | 028617 | 4/2001 |
| WO | 078817 | 10/2001 |
| WO | 030974 | 4/2003 |
| WO | 057604 | 6/2006 |
| WO | 76750 | 5/2013 |

OTHER PUBLICATIONS

Partial European Search Report for EP 19151686.3 issued by the European Patent Office, Jul. 25, 2019: 28 pgs.
Extended European Search Report for EP 19151686.3 issued by the European Patent Office, Oct. 29, 2019:38 pgs.
International Search Report and Written Opinion for PCT/IB2020/050235, issued by the European Patent Office, Apr. 9, 2020; 49 pgs.
International Preliminary Report on Patentability for PCT/IB2020/050235, issued by the European Patent Office, Jul. 12, 2020; 60 pgs.

* cited by examiner

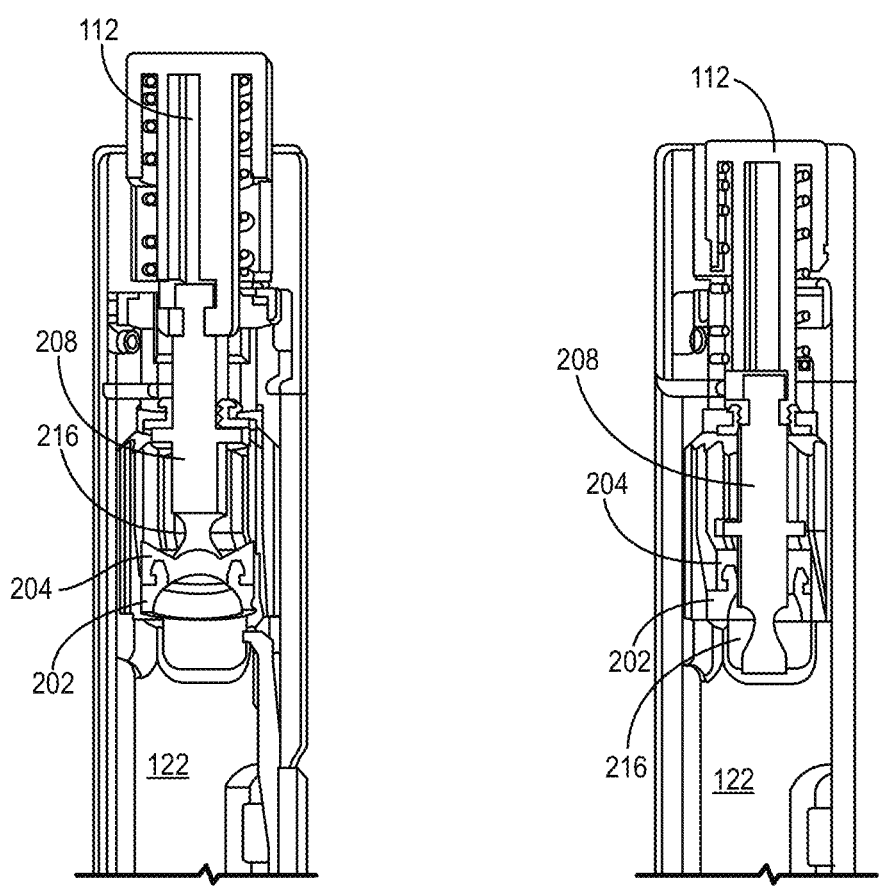
FIG. 11A FIG. 11B

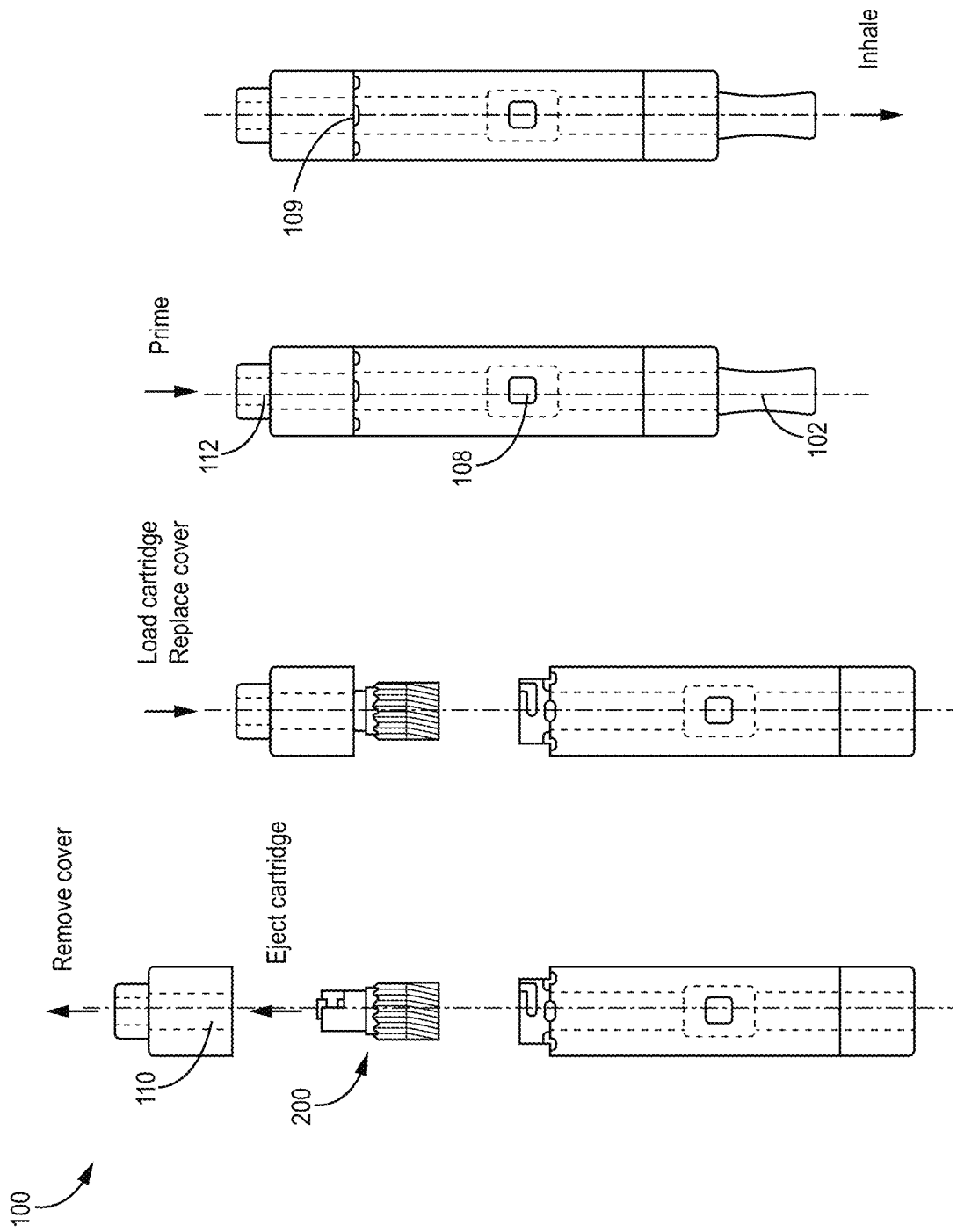

DRY POWDER INHALER

This application is the § 371 U.S. National Stage of International Application No. PCT/IB2020/050235, filed 13 Jan. 2020, which claims the benefit of European Application No. 19151686.3, filed 14 Jan. 2019, the disclosures of which are incorporated by reference herein in their entireties.

BACKGROUND OF THE INVENTION

Due to documented health hazards of traditional tobacco cigarettes to smokers and bystanders, there has been a shift in the marketplace to find suitable alternatives for the delivery of nicotine to the lungs of a subject. It may be desirable to deliver a bioactive material to the lungs of a subject. For example, it may be desirable to deliver nicotine to the subject's lungs without the creation of second-hand smoke, and without the unpleasant odors associated with traditional tobacco smoking. One mechanism to achieve this is via inhalation of a bioactive material as a dry powder formulation. In such systems, a dry powder inhaler is used to deposit the powder on the inner surfaces of the lungs for absorption into the bloodstream. However, many dry powder inhalers have numerous undesirable features.

For example, many devices are designed for medical conditions where a patient requires immediate or complete delivery of a medicament. These devices deliver the medicament in a single inhalation. Thus, these devices are not suitable for medicaments that are preferably delivered over several inhalations. Further, these devices rely on air currents that flow directly through or across the medicament which causes some of the medicament to travel at high speed and impact undesired portions of the subject's airway.

Other devices rely on overly complicated or awkward mechanisms for their use. For example, propellers have been used to rotate a capsule to expel powder by centrifugal force, or various rotating or sliding mechanisms have been used to deposit discrete amounts of powder into the airflow path of an inhaler. These devices are also difficult to use discretely.

An existing device is shown in U.S. Pat. No. 6,234,169 to Bulbrook ("Bulbrook"), which describes a cone shaped device that protrudes into a dry powder storage reservoir to generate a vortex-like effect inside the cone. The device uses the vortex to dip down inside the storage reservoir and pick up a slug of powder and deliver it to the airways of an individual. However, a limitation of the Bulbrook design is that it does not provide adequate energy inside the storage reservoir to deagglomerate the powder sufficiently to deliver the desired aerosol to the user. The Bulbrook design also lacks a reliable method of preventing accidental powder release or a feature for switching storage reservoirs.

It would be desirable to provide a dry powder inhaler that creates sufficient turbulence inside a dry powder chamber such that increased amounts of powder can be picked up into the air for inhalation, while maintaining ease of use in a discrete design.

SUMMARY OF THE INVENTION

In one aspect, the present invention relates to a dry powder inhaler device, including: a cartridge having a proximal end, a distal end, and a grooved exterior, the cartridge being suitable for holding dry powder; a priming button affixed to distal end of the cartridge; a delivery chamber comprising a lumen therethrough, a proximal end, and a distal end, the distal end of the delivery chamber abutting the proximal end of the cartridge; a mouthpiece abutting the proximal end of the delivery chamber, the mouthpiece comprising a lumen fluidly connected to the lumen of the delivery chamber; vortex member positioned between the mouthpiece and the delivery chamber; and an elongate housing comprising a lumen encasing the cartridge, delivery chamber, vortex member, and mouthpiece therein; wherein actuating the priming button deposits dry powder from the cartridge into the lumen of the delivery chamber, and wherein air drawn over the cartridge is angled by the grooved exterior, enters the delivery chamber in a turbulent manner to entrain the dry powder, then passes through the vortex member in a further turbulent manner to be drawn through the lumen of the mouthpiece.

In one embodiment, the housing comprises a cross section with a circular shape, an ovoid shape, or a polygonal shape having three, four, five, or six sides. In one embodiment, the lumen of the mouthpiece further comprises at least one groove, ridge, or fin for increasing the turbulence of air passing therethrough. In one embodiment, the mouthpiece is retractable into the elongate housing. In one embodiment, the mouthpiece is retractable and deployable by a sliding tab running along a track on the elongate housing. In one embodiment, the mouthpiece is retractable and deployable by a spring mechanism within the elongate housing and a release button on the elongate housing. In one embodiment, the mouthpiece retracts into the delivery chamber and blocks the deposition of dry powder into the delivery chamber.

The cartridge may be configured to store an amount of dry powder. The cartridge may contain an amount of dry powder.

The dry powder may comprise a bioactive material. As used herein, the term 'bioactive material' refers to a material which has effect on a living organism, tissue or cell. The bioactive material may comprise a drug. The bioactive material may provide some prophylactic or pharmacologic effect. The bioactive material may comprise at least one physiologically or pharmacologically active substance that produces a localized or systemic effect in a subject.

The bioactive material may comprise at least one of: an antibiotic, an antibody, an antiviral agent, an antiepileptic, an analgesic, an anti-inflammatory agent, and a bronchodilator. The bioactive material may comprise at least on of an inorganic and an organic compound. The bioactive material may be configured to act on at least one of the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autocoid systems, the alimentary and excretory systems, the histamine system, and the central nervous system.

The bioactive material may comprise at least one of: a polysaccharide, a steroid, a hypnotics or sedative, a psychic energizer, a tranquilizer, an anticonvulsant, a muscle relaxant, an antiparkinson agent, a muscle contractant, an antimicrobial, and an antimalarial. The bioactive material may comprise a hormonal agent. For example, the bioactive material may comprise at least one of a contraceptive, a sympathomimetic, a polypeptide, and a protein capable of eliciting physiological effects, a diuretic, a lipid regulating agent, an antiandrogenic agent, an antiparasitic, a neoplastic, an antineoplastic, and a hypoglycemic. The bioactive material may comprise at least one of a nutritional agent and supplements, a growth supplement, a vitamin or a mineral, an antienteritis agent, an electrolyte, and a diagnostic agent.

The bioactive material may comprise at least one of calcitonin, erythropoietin (EPO), Factor VIII, Factor IX, ceredase, cerezyme, cyclosporine, granulocyte colony stimulating factor (GCSF), alpha-I proteinase inhibitor, elcatonin, granulocyte macrophage colony stimulating factor (GMCSF), growth hormone, human growth hormone (hGH), growth hormone releasing hormone (GHRH), heparin, low molecular weight heparin (LMWH), interferon alpha, interferon beta, interferon gamma, interleukin-2, luteinizing hormone releasing hormone (LHRH), leuprolide, somatostatin, somatostatin analogs including octreotide, vasopressin analog, follicle stimulating hormone (FSH), immunoglobulins, insulin-like growth factor, insulintropin, interleukin-I receptor antagonist, interleukin-3, interleukin-4, interleukin-6, macrophage colony stimulating factor (M-CSF), nerve growth factor, parathyroid hormone (PTH), thymosin alpha I, IIb/IIIa inhibitor, alpha-I antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-I receptor, I3-cis retinoic acid, nicotine, nicotine bitartrate, gentamicin, ciprofloxacin, amphotericin, amikacin, tobramycin, pentamidine isethionate, albuterol sulfate, metaproterenol sulfate, beclomethasone dipropionate, triamcinolone acetamide, budesonide acetonide, ipratropium bromide, flunisolide, fluticasone, fluticasone propionate, salmeterol xinofoate, formeterol fumarate, cromolyn sodium, ergotamine tartrate, nicotine and the analogues, agonists and antagonists of the above.

The dry powder inhaler of the present invention may be configured to deliver a bioactive material to a region of a subject's airway. Pulmonary delivery of a bioactive material may be advantageous as it is relatively non-invasive, may avoid the bioactive material first passing through the metabolism of the subject, may allow direct delivery of the bioactive material to the site of action for the treatment of respiratory diseases, and it may allow the bioactive material to be delivered to a large surface area in the airway of a subject.

The dry powder may comprise a prophylactic or therapeutic agent for the treatment and prevention of pulmonary and systemic disorders. Pulmonary disorders may be difficult to be effectively cured through conventional modes of dosage system. The pulmonary and systemic disorders include chronic obstructive pulmonary disease, lung cancer, cystic fibrosis, tuberculosis, and asthma.

The prophylactic or therapeutic agent for the treatment and prevention of pulmonary and systemic disorders may comprise at least one of: a $\beta 2$ adrenergic agonist, a corticosteroid and a cromone, and an anticholinergic. Corticosteroid inhalers (dry-powder or metered-dose inhalers) have become the primary anti-inflammatory treatment for adults and are very widely used in children. Systemically active corticosteroids (e.g. prednisone or dexamethasone) can be inhaled.

The dry powder may comprise at least one of a peptide or a protein. Direct administration to the lungs for local action allows high doses of protein and peptides to be distributed while preventing systemic adverse effects. For example, the dry powder may comprise at least one of insulin, human growth hormone (hGH), calcitonin, and parathyroid. These may be used to treat diabetes, hormone deficiency, and osteoporosis, respectively. Other examples include but are not limited to recombinant human granulocyte colony stimulating factor to treat bone disorders.

The dry powder may comprise at least one antibiotic. For example, the dry powder may comprise tobramycin as maintenance therapy for cystic fibrosis (CF) patients with chronic Pseudomonas aeruginosa infection.

The dry powder may comprise at least one vaccine. The vaccine may be a prophylactic or a therapeutic vaccine. For example, the dry powder may comprise inulin-stabilized influenza subunit vaccine prepared by spray-freeze drying to induce systemic, mucosal humoral as well as cell-mediated immune responses.

The dry powder may comprise nicotine. As used herein, the term "nicotine" refers to nicotine and nicotine derivatives in any form, including but not limited to, a free-base nicotine, nicotine salt, or in a matrix such as a sugar matrix or organometallic complex. Nicotine salts may include nicotine lactate, nicotine bitartrate, and the like.

In another aspect, the present invention relates to a dry powder cartridge, comprising: a cylindrical body comprising a lumen having a proximal opening at a proximal end and a distal opening at a distal end and a longitudinal axis therethrough; a reservoir at the proximal end of the cylindrical body fluidly connected to the lumen; and a moveable spindle having a proximal end and a distal end and positioned within the lumen and reservoir of the body, the spindle movable along the longitudinal axis of the cylindrical body, the moveable spindle comprising at least one groove near its proximal end; wherein the at least one groove is configured to slideably pass from the reservoir through the proximal opening of the body.

In one embodiment, the cylindrical body comprises an exterior surface having at least one groove. In one embodiment, the cartridge delivers a dose amount controlled by the size of the at least one groove near the proximal end of the moveable spindle. In one embodiment, the spindle is engageable and moveable with the priming button of a dry powder inhaler. In one embodiment, any gaps between the moveable spindle and the cylindrical body are sealed with at least one gasket. In one embodiment, the cartridge is disposable.

In another aspect, the present invention relates to a method of delivering dry powder to a subject, the method comprising the steps of: providing a dry powder inhaler device comprising a cartridge containing dry powder, a priming button, a delivery chamber, a mouthpiece, and an elongate housing encasing the cartridge, delivery chamber, and mouthpiece therein; depressing the priming button to deposit an amount of dry powder from the cartridge into the delivery chamber; and applying a vacuum to the mouthpiece; wherein the vacuum draws air into the delivery chamber to entrain the dry powder into the air, and wherein the vacuum draws the air with entrained dry powder through the mouthpiece and into the subject.

In one embodiment, the cartridge is selected based upon the amount of dry powder delivered with a single depression of the priming button. In one embodiment, the priming button is depressed a plurality of times to increase the amount of delivered dry powder.

In another aspect, the present invention relates to kit for delivering dry powder, the kit comprising a dry powder inhaler device comprising a cartridge, a priming button, a delivery chamber, a mouthpiece, and an elongate housing encasing the cartridge, delivery chamber, and mouthpiece therein.

In one embodiment, the kit further comprises additional cartridges. In one embodiment, the kit further comprises instructional material for using the dry powder inhaler device.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 11A and FIG. 11B depict close up cutaway views of an exemplary DPI device demonstrating an exemplary priming mechanism.

FIG. 13A through FIG. 13D depict various diagrams demonstrating an exemplary cartridge changing method for an exemplary DPI device.

DETAILED DESCRIPTION

The present invention provides in part dry powder inhaler (DPI) devices for dispensing dry powder and methods for using the same. The DPI devices feature vortex mechanisms for changing the direction of airflow to entrain an amount of a dry powder dose for delivery into a user's lungs. The DPI devices feature replaceable dry powder cartridges. The DPI devices also feature a retractable configuration for storage and for accidental dispensing of dry powder. The DPI devices are able to dispense dry powder in controlled dosages.

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements or steps are desirable or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

Figure 1:
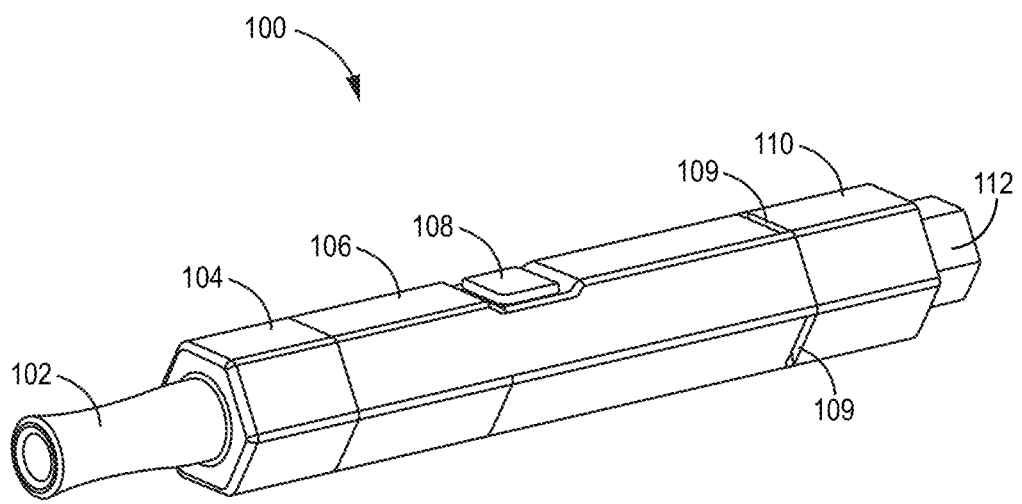
FIG. 1 depicts an isometric view of an exemplary dry powder inhaler (DPI) device.

Referring now to FIG. 1, the exterior of an exemplary dry powder inhaler (DPI) device 100 is depicted. DPI device 100 comprises mouthpiece 102, mouth cap 104, sleeve or exterior housing 106, mouthpiece release button 108, airflow openings 109, priming button cap 110, and priming button 112.

Figure 2:
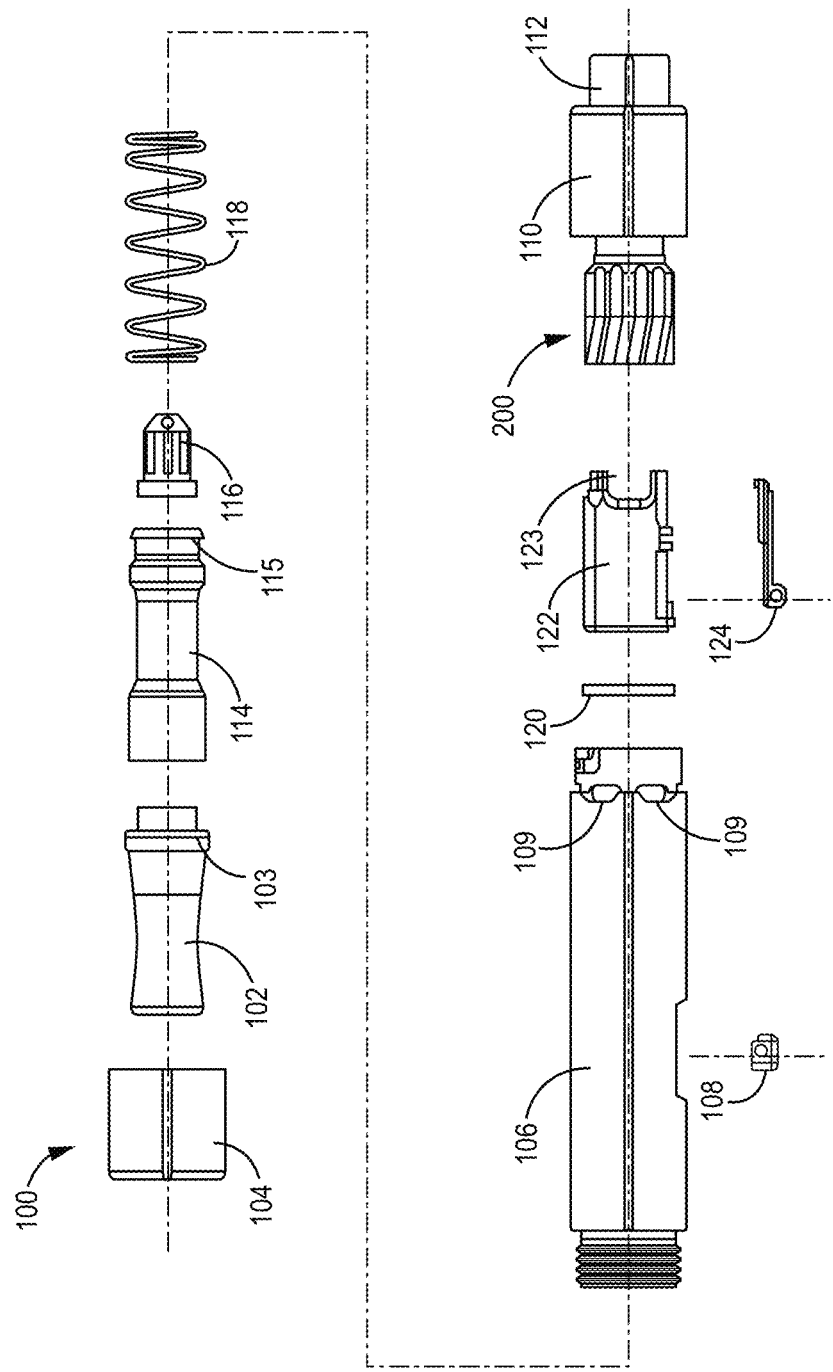
FIG. 2 depicts an exploded view of the proximal components of an exemplary DPI device.

Referring now to FIG. 2, the internal proximal components of an exemplary DPI device 100 are detailed. The exemplary DPI device 100 features a vortex mechanism that includes cyclone chamber 114, vortex member 116, mouthpiece spring 118, gasket 120, delivery chamber 122, latch 124, and cartridge 200.

Figure 3:
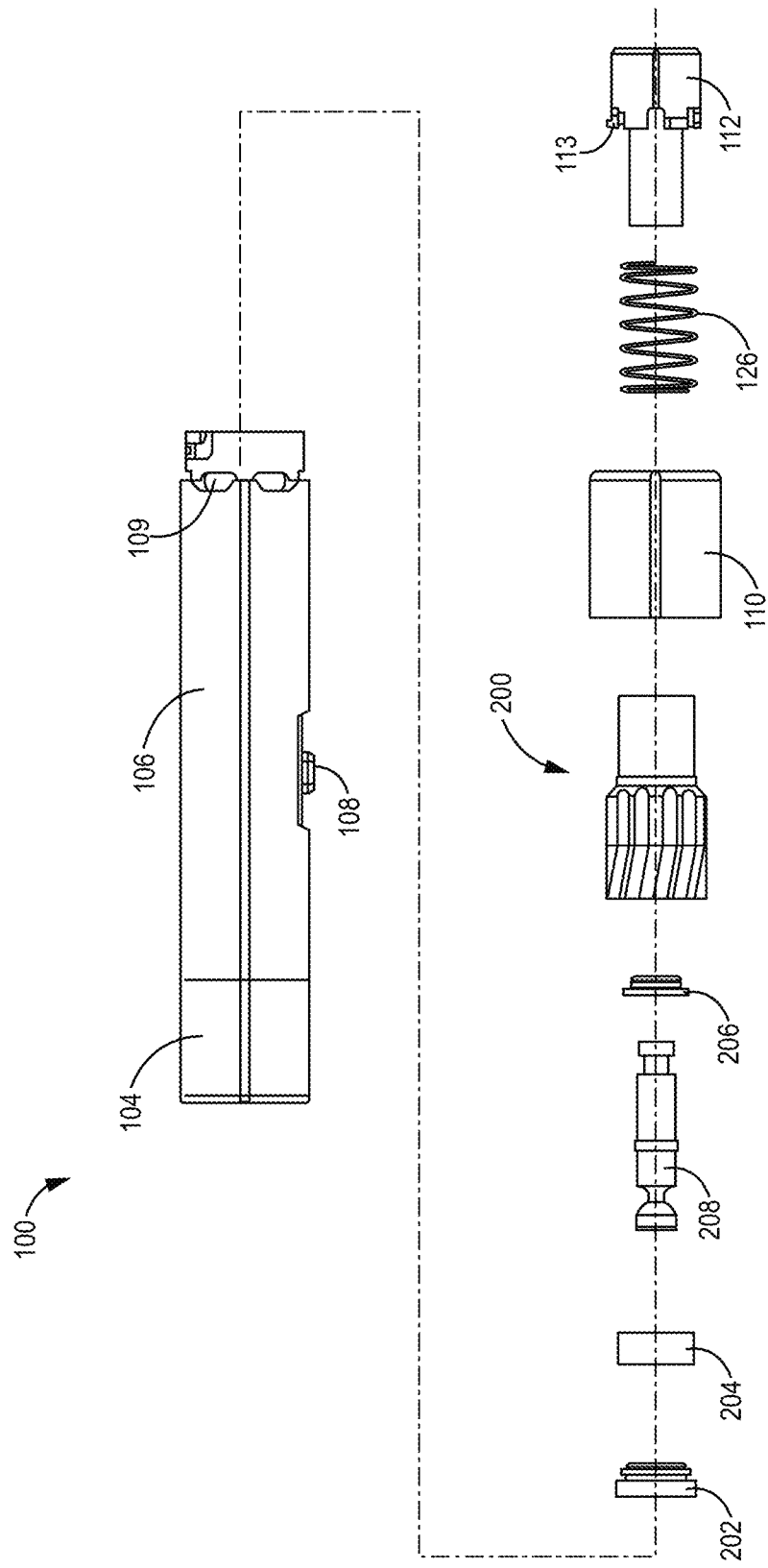
FIG. 3 depicts an exploded view of the distal components of an exemplary DPI device.

Referring now to FIG. 3, the internal distal components of an exemplary DPI device 100 are detailed, including first cartridge gasket 202, second cartridge gasket 204, third cartridge gasket 206, spindle 208, and priming spring 126.

Figure 4:
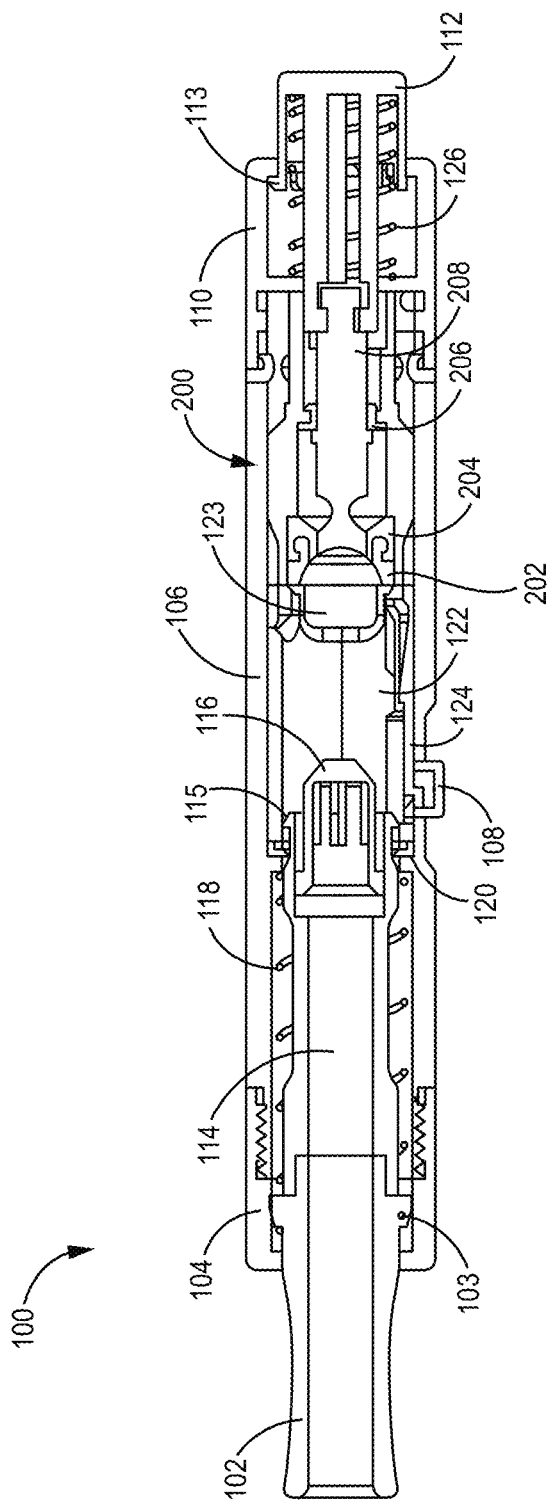
FIG. 4 depicts a cross section view of an exemplary DPI device.

Referring now to FIG. 4, a cross section view of an exemplary DPI device 100 is shown, demonstrating the arrangement of the several components. The construction of the several components can be made from any suitable material, such as plastic or metal. In certain embodiments, certain components may comprise additional materials where noted.

Housing 106 houses the several internal components. Housing 106 comprises an elongate tubular shape having a lumen throughout. At its distal end, housing 106 comprises at least one airflow opening 109. In certain embodiments, housing 106 may comprise a slot for mouthpiece release button 108, which may further comprise an indentation around said slot for ease of access to mouthpiece release button 108. The exterior of housing 106 may be any suitable shape, including rounded shapes and faceted shapes. The shape of housing 106 may be described from the shape of its cross section. For example, when viewed head on, housing 106 may have a circular cross section, an ovoid cross section, or a polygonal cross section having three, four, or more sides. In some embodiments, housing 106 may further comprise external features for enhancing grip, such as one or more ridges, grooves, bumps, and the like. Housing 106 may comprise any suitable material, such as metals, plastics, and wooden materials.

Mouthpiece 102 inserts into the proximal end of housing 106. In some embodiments, mouthpiece 102 comprises a tubular shape having a lumen suitable for passing air and entrained particles. In some embodiments, the lumen of mouthpiece 102 further comprises features to enhance airflow turbulence, such as one or more grooves, ridges, fins, and the like. In some embodiments, mouthpiece 102 comprises an exterior surface suitably contoured to a user's mouth. Mouthpiece 102 further comprises flange 103 at its distal end.

Mouth cap 104 attaches to the proximal end of housing 106 to secure mouthpiece 102 at least partially within housing 106. Mouth cap 104 can have any suitable shape, including rounded shapes and faceted shapes. In some embodiments, mouth cap 104 comprises the same cross section shape as housing 106. Mouth cap 104 can attach by any suitable means, such as by mated male and female threads (FIG. 4), a peg and slot system, a friction fit system, and the like. Mouth cap 104 comprises an aperture sized to allow mouthpiece 102 to pass through but not flange 103, thereby preventing mouthpiece 102 from completely exiting housing 106.

Cyclone chamber 114 attaches to the distal end of mouthpiece 102. Cyclone chamber 114 comprises a tubular shape having a lumen fluidly connected to the lumen of mouthpiece 102, also suitable for passing air and entrained particles. In some embodiments, the lumen of cyclone chamber 114 further comprises features to enhance airflow turbulence, such as one or more grooves, ridges, fins, and the like. Cyclone chamber 114 further comprises flange 115 at its distal end.

Vortex member 116 attaches to the distal end of cyclone chamber 114. Vortex member 116 comprises at least one channel for directing air and entrained particles. In some embodiments, the at least one channel may be angled or curved to enhance airflow turbulence.

Figure 5:
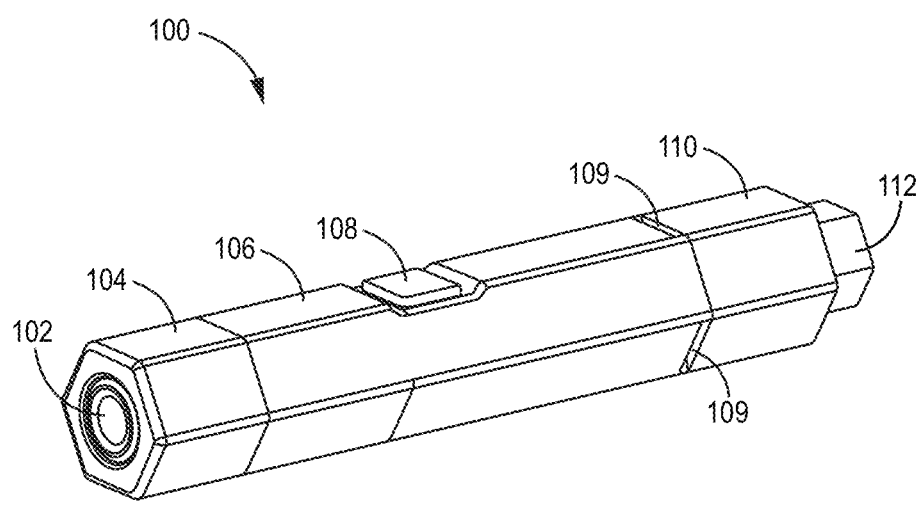
FIG. 5 depicts an exemplary DPI device with a retracted mouthpiece.

In some embodiments, mouthpiece 102, cyclone chamber 114, and vortex member 116 are slideable as a single unit within the lumen of housing 106. Referring now to FIG. 5, mouthpiece 102 may slide into housing 106 to a retracted position such that the proximal end of mouthpiece 102 is flush with or recessed within the proximal end of mouth cap 104. In some embodiments, mouthpiece spring 118 provides proximal movement to mouthpiece 102, wherein mouthpiece spring 118 exerts a spring force against flange 103 (FIG. 4).

Delivery chamber 122 is situated near the center of housing 106. The external dimensions of delivery chamber 122 are sized to fit within the lumen of housing 106. Delivery chamber 122 comprises a cavity sized to at least partially fit cyclone chamber 114 and vortex member 116. For example, in some embodiments, cyclone chamber 114, and vortex member 116 may be at least partially retracted into the cavity of delivery chamber 122 (FIG. 5), while in other embodiments, the cavity of delivery chamber 122 is clear of obstructions (FIG. 4). In some embodiments, delivery chamber 122 comprises airway openings 123 to permit air to flow into the cavity of delivery chamber 122.

Figure 6:
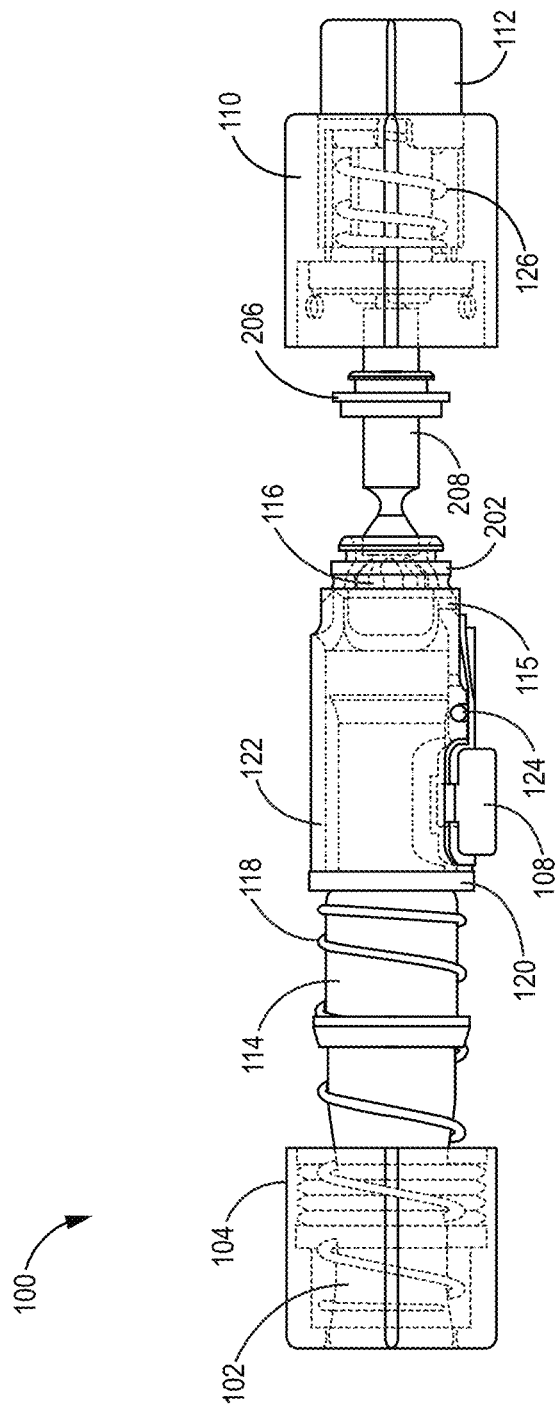
FIG. 6 depicts a cutaway view of an exemplary DPI device with a retracted mouthpiece.

In certain embodiments, delivery chamber 122 comprises slots to fit mouthpiece release button 108 and latch 124. Mouthpiece release button 108 attaches to and actuates latch 124. Latch 124 engages with flange 115 of cyclone chamber 114 to secure cyclone chamber 114 in a retracted position (FIG. 6).

Figure 7A:
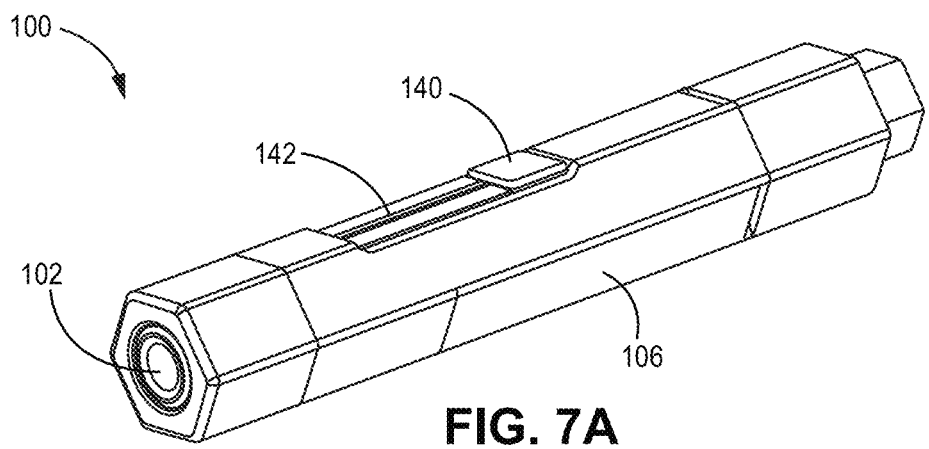
FIG. 7A through FIG. 7C depict various views of an exemplary DPI device having a sliding tab and track mechanism.
Figure 7B:
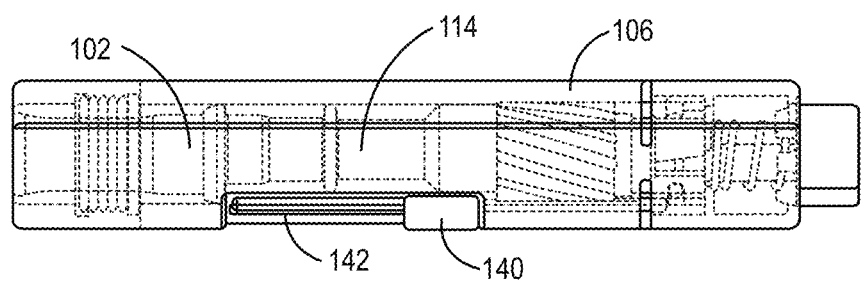
Figure 7C:
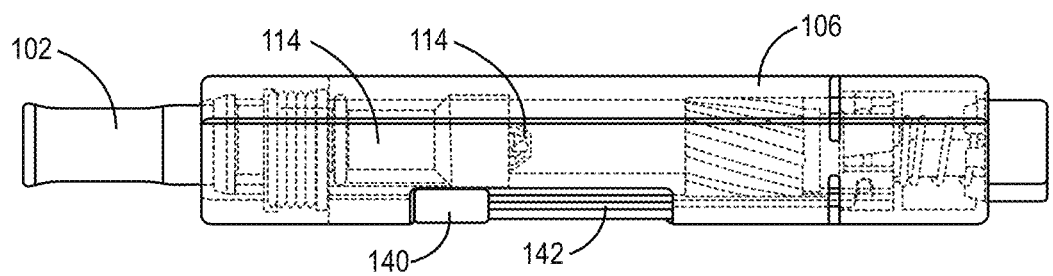

As shown in FIG. 7A through FIG. 7C, in some embodiments, a sliding tab 140 is provided, wherein sliding tab 140 is slideable along track 142 on housing 106. Sliding tab 140 is attached to mouthpiece 102, cyclone chamber 114, and vortex member 116, whereby moving sliding tab 140 along track 142 slides the three components in and out of housing 106.

In certain embodiments, the sliding mechanism may further comprise a spring (not pictured). In one embodiment, the spring exerts a force that compels mouthpiece 102 to deploy out of housing 106. In another embodiment, the spring exerts a force that compels mouthpiece 102 to retract into housing 106. In certain embodiments, sliding tab 140 further comprises at least one locking mechanism, such that when sliding tab 140 slides mouthpiece 102 against the spring force, the locking mechanism may temporarily lock mouthpiece 102 in place.

Gasket 120 is provided at the proximal end of delivery chamber 122. In some embodiments, gasket 120 comprises an inner diameter sized to fit the external diameter of cyclone chamber 114 such that gasket 120 maintains a seal with cyclone chamber 114 as cyclone chamber 114 slides within housing 106 and delivery chamber 122. Gasket 120 may comprise any suitable gasket material, such as a plastic, rubber, silicon, or other elastic material.

Figure 8A:
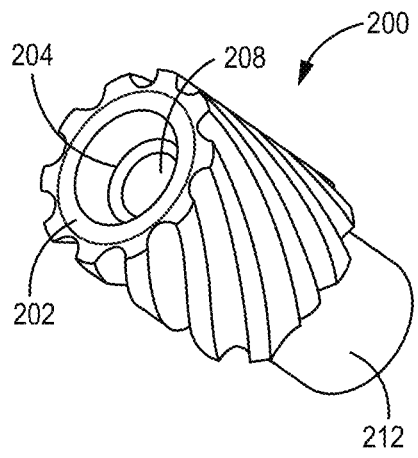
FIG. 8A through FIG. 8C depict various views of the components of an exemplary DPI device cartridge.
Figure 8B:
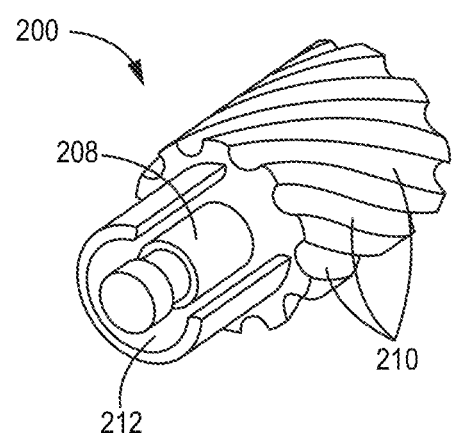
Figure 8C:
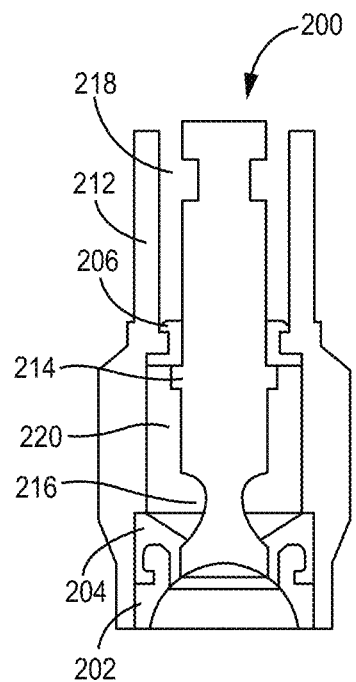

Cartridge 200 abuts the distal end of delivery chamber 122 within housing 106. Referring now to FIG. 8A through FIG. 8C, an exemplary cartridge 200 is depicted. Cartridge 200 comprises first cartridge gasket 202, second cartridge gasket 204, third cartridge gasket 206, and spindle 208. Cartridge 200 is substantially cylindrical, having a longitudinal axis, an inner reservoir 220 for holding dry powder, and an exterior surface. Cartridge 200 further comprises an aperture at its proximal and distal ends.

In some embodiments, the exterior surface of cartridge 200 comprises a region of angled vortex grooves 210 (FIG. 8A and FIG. 8B). In other embodiments, the exterior surface of cartridge 200 comprises at least one region of substantially straight vortex grooves 210 and at least one region of angled vortex grooves 210 (FIG. 10C).

Spindle 208 is substantially cylindrical and comprises delivery ring groove 216 near its proximal end, priming ring groove 218 near its distal end, and stopper flange 214 near its center. Delivery ring groove 216 holds an amount of dry powder delivered in a single dose, and may comprise a plurality of sizes and volumes. Spindle 208 is positioned within the apertures of cartridge 200, wherein spindle 208 is aligned with the longitudinal axis of cartridge 200. The distal end of spindle 208 protrudes out from the distal aperture of cartridge 200. In some embodiments, at least one sheath 212 is provided at the distal end of cartridge 200 to prevent inadvertent depression of spindle 208.

First cartridge gasket 202 and second cartridge gasket 204 seal the space between the proximal aperture of cartridge 200 and spindle 208 passing therethrough. Third cartridge gasket 206 seals the space between the distal aperture of cartridge 200 and spindle 208 passing therethrough. Second cartridge gasket 204 and third cartridge gasket 206 restricts proximal and distal movement of spindle 208, respectively, by blocking stopper flange 214.

In some embodiments, first cartridge gasket 202 is sized to accommodate the dimensions of vortex member 116. For example, a vortex member 116 in a retracted position may fit within first cartridge gasket 202 (FIG. 6). First cartridge gasket 202, second cartridge gasket 204, and third cartridge gasket 206 may comprise any suitable gasket material, such as a plastic, rubber, silicon, or other elastic material.

The distal end of DPI device 100 is capped by the priming assembly, comprising priming button 112, priming button cap 110, and priming spring 126. Priming button 112 inserts into the distal end of housing 106. Priming button 112 can comprise any suitable shape, including rounded shapes and faceted shapes. In some embodiments, priming button 112 comprises the same cross section shape as housing 106.

Figure 9A:
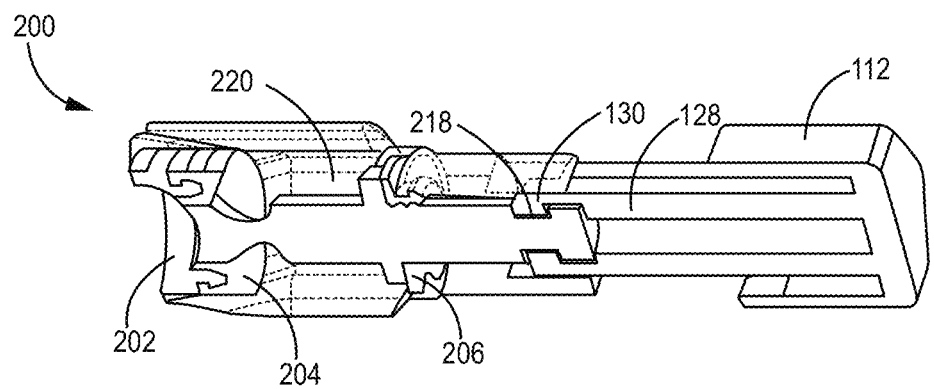
FIG. 9A and FIG. 9B depict various views of an exemplary DPI device cartridge and priming button assembly.
Figure 9B:
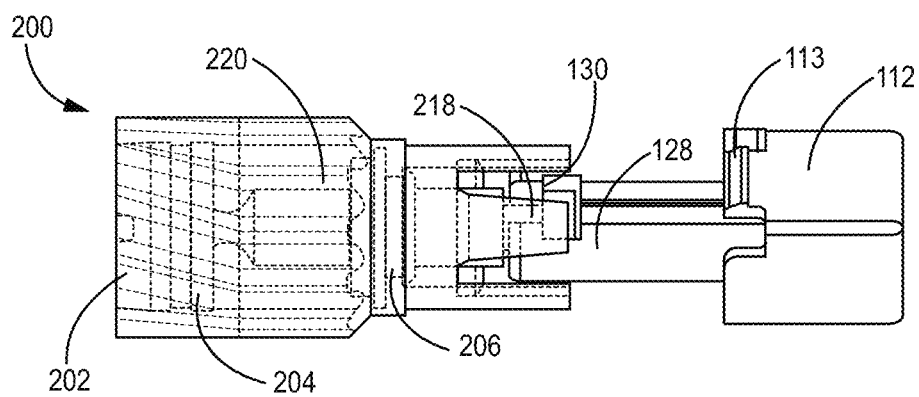

Referring now to FIG. 9A and FIG. 9B, a series of diagrams are depicted illustrating the connection between priming button 112 and cartridge 200. Priming button 112 further comprises tab 113, and priming button shaft 128 with priming ring slot 130. Priming ring slot 130 is shaped to fit priming ring groove 218 on the distal end of spindle 208. In certain embodiments, priming button shaft 128 is dimensioned to fit between the at least one sheath 212 to engage priming ring slot 130 to priming ring groove 218.

Priming cap 110 attaches to the distal end of housing 106 to secure priming button 112 at least partially within housing 106. Priming cap 110 can have any suitable shape, including rounded shapes and faceted shapes. In some embodiments, priming cap 110 comprise the same cross section shape as housing 106. Priming cap 110 can attach by any suitable means, such as by mated male and female threads, a peg and slot system (FIG. 11), a friction fit system, and the like. Priming cap 110 comprises an aperture sized to allow priming button 112 to pass through but not the at least one tab 113, thereby preventing priming button 112 from completely exiting housing 106.

In some embodiments, priming spring 126 provides distal movement to priming button 112, wherein priming spring 126 exerts a spring force against the interior of priming button 112 (FIG. 4).

DPI device 100 comprises two configurations: a deployed configuration (FIG. 1, FIG. 4) and a retracted configuration (FIG. 5, FIG. 6). In the deployed configuration, mouthpiece 102, cyclone chamber 114, and vortex member 116 are fully extended out of DPI device 100. The cavity of delivery chamber 122 is clear of obstructions. In some embodiments, the deployed configuration is maintained by the spring force exerted upon flange 103 of mouthpiece 102.

In the retracted configuration, mouthpiece 102, cyclone chamber 114, and vortex member 116 are fully withdrawn into DPI device 100. As described elsewhere herein, in a retracted configuration, the proximal end of mouthpiece 102 is flush with or recessed within the proximal end of DPI device 100. Cyclone chamber 114 and vortex member 116 are at least partially withdrawn into the cavity of delivery chamber 122. In some embodiments, the retracted configuration is maintained by latch 124 engaging and holding the at least one flange 115 of cyclone chamber 114. The distal end of vortex member 116 is seated within first cartridge gasket 202, abutting against the proximal end of spindle 208 and preventing spindle 208 from being depressed by priming button 112.

In some embodiments, DPI device 100 can be switched from the deployed configuration to the retracted configuration by applying a force against the proximal end of mouthpiece 102. The force must be sufficient to counteract the spring force of mouthpiece spring 118 to allow mouthpiece 102, cyclone chamber 114, and vortex member 116 to retreat into housing 106. When the at least one flange 115 passes under latch 124, latch 124 engages and holds mouthpiece 102, cyclone chamber 114, and vortex member 116 in the retracted configuration. In some embodiments, an auditory signal such as a click indicates latch 124 has engaged the at least one flange 115.

In some embodiments, DPI device 100 can be switched from the retracted configuration to the deployed configuration by depressing mouthpiece release button 108. Depressing mouthpiece release button 108 disengages latch 124 from the at least one flange 115, allowing the spring force from mouthpiece spring 118 to push flange 103, which in turn fully extends mouthpiece 102, cyclone chamber 114, and vortex member 116.

Referring now to FIG. 7A through FIG. 7C, in some embodiments DPI device 100 can be switched between a deployed configuration and a retracted configuration by moving sliding tab 140 along track 142.

DPI device 100 is primed to prepare a dose of dry powder for delivery. The dose of dry powder may be selected before priming, wherein a user selects a cartridge 200 or a spindle 208 with a delivery ring groove 216 for delivering a specific amount of powder per dose.

Figure 10A:
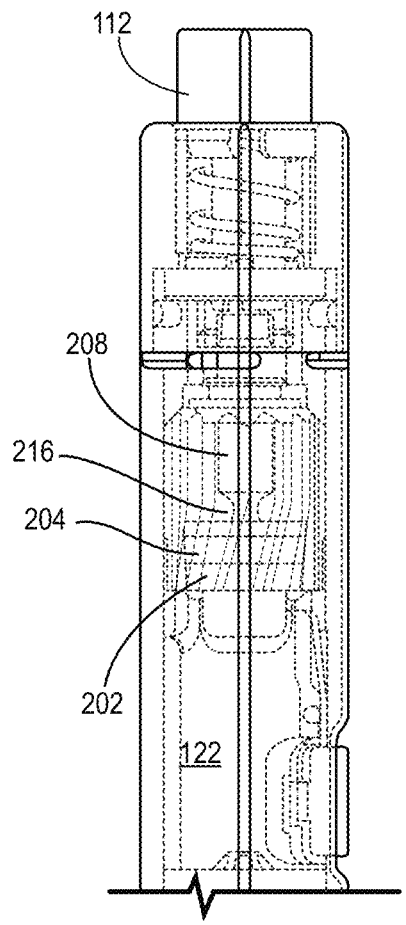
FIG. 10A through FIG. 10C depict various close-up views of an exemplary DPI device demonstrating an exemplary priming mechanism.

Referring now to FIG. 10A through 10O, diagrams illustrating an exemplary priming mechanism are depicted. FIG. 10A depicts the priming assembly, cartridge 200, and delivery chamber 122 prior to the priming step. Priming button 112 is fully extended by a spring force exerted upon it from priming spring 126. Spindle 208 is in a distal position, positioning delivery ring groove 216 within reservoir 220 (cutaway view in FIG. 11A). Reservoir 220 comprises the dry powder, which fills in the space offered by delivery ring groove 216.

Figure 10B:
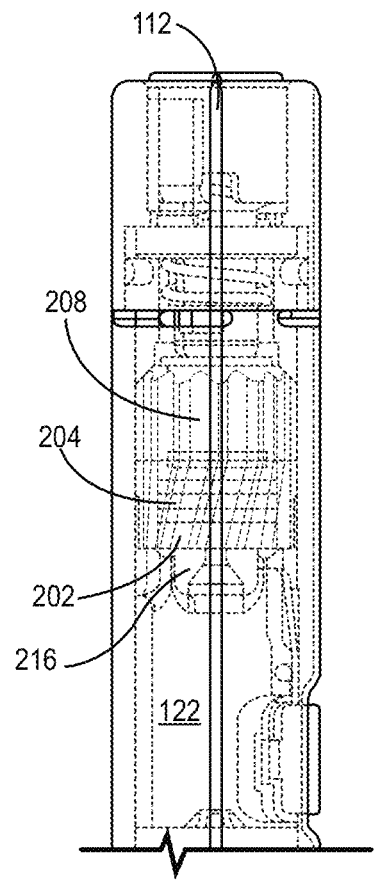
Figure 10C:
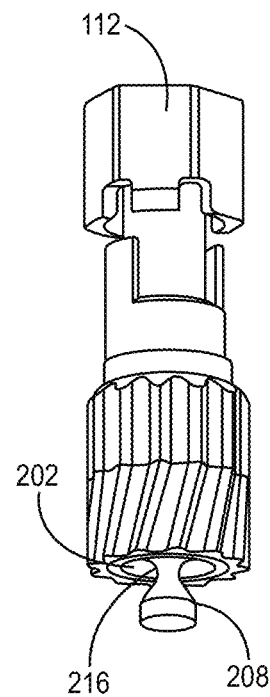

FIG. 10B depicts the priming step, whereupon priming button 112 is depressed. The proximal movement of priming button 112 in turn pushes spindle 208 in a proximal direction, positioning delivery ring groove 216 outside of reservoir 220 and into delivery chamber 122 (cutaway view in FIG. 11B), whereupon the dry powder carried within delivery ring groove 216 deposits into delivery chamber 122 by gravity. FIG. 10C provides an unobstructed view of the delivery ring groove 216 positioned outside of reservoir 220.

After the priming step, priming button 112 is released. Priming spring 126 is then able to push priming button 112 in a distal direction to its extended position depicted in FIG. 10A. The distal movement of priming button 112 in turn retracts spindle 208 in a distal direction, repositioning delivery ring groove 216 within reservoir 220, whereupon dry powder may refill the space offered by delivery ring groove 216.

In some embodiments, a single priming step fully depresses priming button 112 to deposit a single dose in delivery chamber 122. In some embodiments, the priming step may be repeated to provide a larger dose in delivery chamber 122. In some embodiments, priming button 112 comprises a plurality of stepped positions between the fully extended position and the fully depressed position, wherein each stepped position correlates to a dose amount.

Figure 12:
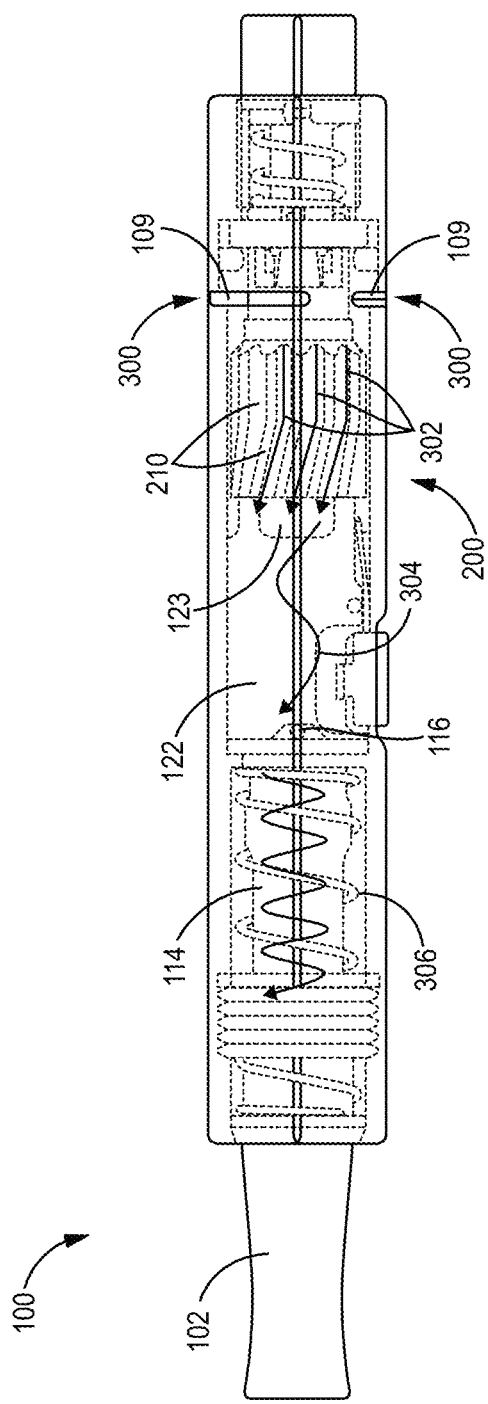
FIG. 12 depicts a diagram demonstrating the flow of air through an exemplary DPI device.

Referring now to FIG. 12, a diagram depicting an airflow pathway through an exemplary DPI device 100 is depicted. Airflow is initiated by a user applying a vacuum upon mouthpiece 102, such as by inhalation. The air follows a first air path 300 by entering DPI device 100 through the plurality of airflow openings 109. The air then follows a second air path 302 by flowing through the at least one vortex groove 210 on the exterior of cartridge 200, wherein the at least one vortex groove 210 angles the flow of air for turbulent air flow.

The turbulent air enters delivery chamber 122 through the at least one airflow opening 123, wherein dry powder present in delivery chamber 122 becomes entrained by the turbulent air. The turbulent air with entrained dry powder then follows air path 304 through at least one channel in vortex member 116 to enter cyclone chamber 114, wherein the at least one channel in vortex member 116 provides a sharper angle to the flow of air. The turbulent air with entrained dry powder then follows air path 306 to pass through cyclone chamber 114, mouthpiece 102, and into the user.

Referring now to FIG. 13A through FIG. 13D, a series of diagrams illustrating an exemplary method of exchanging cartridges in a DPI device 100 is depicted. Exchanging cartridges is performed by first disengaging priming button cap 110 from DPI device 100. Cartridge 200 is extracted from DPI device 100 due to the mating connection between priming ring groove 218 and priming ring slot 130, as described elsewhere herein. Cartridge 200 is separated from priming button shaft 128 and a new cartridge 200 is joined to priming button shaft 128 by mating the connection between priming ring groove 218 and priming ring slot 130. The new cartridge 200 is inserted into DPI device 100 and priming button cap 110 is reengaged to DPI device 100.

The devices of the present invention can be made using any suitable method known in the art. The method of making may vary depending on the materials used. For example, devices substantially comprising a metal may be milled from a larger block of metal or may be cast from molten metal. Likewise, devices substantially comprising a plastic or polymer may be milled from a larger block or injection molded. In some embodiments, the devices may be made using 3D printing techniques commonly used in the art.

The present invention provides methods of dispensing dry powder to a user using a DPI device.

Prior to dispensing dry powder, mouthpiece 102 must first be released by depressing mouthpiece release button 108. Releasing mouthpiece 102 clears delivery chamber 122 for accepting dry powder. As described elsewhere herein, at least one dose of dry powder is deposited into delivery chamber 122 by actuating priming button 112. A user may then inhale the dry powder in the delivery chamber 122 by applying a vacuum to mouthpiece 102, wherein air entering airflow openings 109 entrains the dry powder in delivery chamber 122 and exits through mouthpiece 102, into the user's lungs.

The user may administer further doses by repeating the steps of actuating priming button 112 and inhaling the deposited dry powder dose as desired. When the user has completed administering doses of dry powder, DPI device 100 may be prepared for storage by pressing mouthpiece 102 into DPI device 100 until mouthpiece 102 locks into place, simultaneously compacting the size of the device and arresting the movement of priming button 112 to prevent dry powder leakage.

The present invention provides a kit comprising the devices described herein for use in dispensing dry powder. In certain embodiments, the kit comprises at least one DPI device, such as DPI device 100 of FIG. 1. In certain embodiments, the kit may optionally include other components such as one or more cartridges 200. In certain embodiments, the kit comprises instructional material. Instructional material may include a publication, a recording, a diagram, or any other medium of expression which can be used to communicate the usefulness of any of the devices described herein. The instructional material may also include description of one or more steps to perform any of the methods described herein. The instructional material of the kit may, for example, be affixed to a package which contains one or more kits or devices. Alternatively, the instructional material may be shipped separately from the package, or may be available electronically, such as accessible from the Internet, or any downloadable electronic document file format.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A dry powder inhaler device, comprising:

a cartridge having a proximal end, a distal end, and a grooved exterior surface, the cartridge being suitable for holding dry powder;

a priming button affixed to the distal end of the cartridge;

a delivery chamber comprising a lumen therethrough, a proximal end, and a distal end, the distal end of the delivery chamber abutting the proximal end of the cartridge;

a mouthpiece abutting the proximal end of the delivery chamber, the mouthpiece comprising a lumen fluidly connected to the lumen of the delivery chamber;

a vortex member positioned between the mouthpiece and the delivery chamber; and an elongate housing comprising a lumen encasing the cartridge, delivery chamber, vortex member, and mouthpiece therein, the cartridge grooved exterior surface and the elongate housing define air channels therebetween that extend along the grooved exterior surface of the cartridge; wherein actuating the priming button deposits the dry powder from the cartridge into the lumen of the delivery chamber, and wherein the device is configured such that, in use, air is drawn over the cartridge, angled by the air channels, and enters the delivery chamber in a turbulent manner to entrain the dry powder, then passes through the vortex member in a further turbulent manner to be drawn through the lumen of the mouthpiece.

2. The device of claim 1, wherein the elongate housing comprises a cross section with a circular shape, an ovoid shape, or a polygonal shape having three, four, five, or six sides.

3. The device of claim 1, wherein the lumen of the mouthpiece further comprises at least one groove, ridge, or fin for increasing turbulence of air passing therethrough.

4. The device of claim 1, wherein the mouthpiece is retractable into the elongate housing.

5. The device of claim 4, wherein the mouthpiece is retractable and deployable by a sliding tab running along a track on the elongate housing.

6. The device of claim 4, wherein the mouthpiece is retractable and deployable by a mouthpiece spring within the elongate housing and a release button on the elongate housing.

7. The device of claim 4, wherein the mouthpiece is configured to retract into the delivery chamber and block the deposition of the dry powder into the delivery chamber.

8. The device of claim 1, further comprising a mouthpiece release button.

9. The device of claim 8, wherein the elongate housing further comprises a slot for the mouthpiece release button.

10. The device of claim 9, wherein the dry powder inhaler device is configured to be switched from a retracted configuration to a deployed configuration by depressing the mouthpiece release button.

11. The device of claim 1, further comprising a cyclone chamber attached to a distal end of the mouthpiece.

12. The device of claim 11, wherein a lumen of the cyclone chamber further comprises one or more features to enhance airflow turbulence, wherein the one or more features comprise one or more grooves, ridges, fins, or combination thereof.

13. A dry powder cartridge, comprising:

a cylindrical body comprising a lumen having a proximal opening at a proximal end, a distal opening at a distal end, a longitudinal axis therethrough, and a grooved exterior surface;

a reservoir at the proximal end of the cylindrical body fluidly connected to the lumen; and a moveable spindle having a proximal end and a distal end and positioned within the lumen and reservoir of the body, the distal end of the moveable spindle protrudes out from the distal opening of the cylindrical body, the spindle movable along the longitudinal axis of the cylindrical body, the moveable spindle comprising at least one groove near its proximal end and a stopper flange near a center of the moveable spindle;

wherein the at least one groove is configured to slideably pass from the reservoir through the proximal opening of the body;

a first cartridge gasket and a second cartridge gasket configured to seal a space between the proximal opening of the cylindrical body and the moveable spindle passing therethrough;

a third cartridge gasket configured to seal a space between the distal opening of the cylindrical body and the moveable spindle passing therethrough;

wherein the second cartridge gasket and the third cartridge gasket are configured to restrict proximal and distal movement of the moveable spindle, respectively, by blocking the stopper flange.

14. The dry powder cartridge of claim 13, wherein the dry powder cartridge is configured to deliver a dose amount controlled by the size of the at least one groove near the proximal end of the moveable spindle.

15. The dry powder cartridge of claim 13, wherein the spindle is engageable and moveable with a priming button of a dry powder inhaler.

16. A kit for delivering dry powder, the kit comprising:
a dry powder inhaler device comprising:
the dry powder cartridge as in claim 13,
a priming button,
a delivery chamber,
a mouthpiece, and
an elongate housing encasing the dry powder cartridge, the delivery chamber, and the mouthpiece therein.

17. A method of delivering dry powder to a subject, the method comprising:
providing a dry powder inhaler device comprising a cartridge containing dry powder and having a grooved exterior surface extending along a length of the cartridge, a priming button, a delivery chamber, a mouthpiece, and an elongate housing encasing the cartridge, the delivery chamber, and the mouthpiece therein, the cartridge grooved exterior surface and the elongate housing define air channels therebetween that extend along the exterior surface of the cartridge; depressing the priming button to deposit an amount of the dry powder from the cartridge into the delivery chamber; and applying a vacuum to the mouthpiece; wherein the vacuum draws air over the grooved exterior surface of the cartridge and the air is angled by the air channels to enter into the delivery chamber in a turbulent manner to entrain the dry powder into the air, and wherein the vacuum draws the air with entrained dry powder through the mouthpiece and into the subject.

18. The method of claim 17, wherein the cartridge is selected based upon the amount of dry powder delivered with a single depression of the priming button.

19. The method of claim 17, wherein the priming button is depressed a plurality of times to increase the amount of delivered dry powder.

* * * * *